United States Patent
Wettling et al.

(10) Patent No.: US 11,072,570 B2
(45) Date of Patent: Jul. 27, 2021

(54) PROCESS FOR CONTINUOUSLY PREPARING POLYISOBUTYLENE

(71) Applicant: BASF SE, Ludwigshafen am Rhein (DE)

(72) Inventors: Thomas Wettling, Limburgerhof (DE); Stefan Hirsch, Neustadt (DE); Markus Brym, Limburgerhof (DE); Markus Weis, Roemerberg (DE)

(73) Assignee: BASF SE, Ludwigshafen (DE)

(*) Notice: Subject to any disclaimer, the term of this patent is extended or adjusted under 35 U.S.C. 154(b) by 274 days.

(21) Appl. No.: 13/735,385

(22) Filed: Jan. 7, 2013

(65) Prior Publication Data

US 2013/0178679 A1 Jul. 11, 2013

Related U.S. Application Data

(60) Provisional application No. 61/584,322, filed on Jan. 9, 2012.

(51) Int. Cl.
*C07C 2/02* (2006.01)
*C08F 110/10* (2006.01)

(52) U.S. Cl.
CPC .............. *C07C 2/02* (2013.01); *C08F 110/10* (2013.01)

(58) Field of Classification Search
CPC ................................ C07C 2/02; C08F 10/10
USPC .................................................. 585/521, 502
See application file for complete search history.

(56) References Cited

U.S. PATENT DOCUMENTS

| | | | |
|---|---|---|---|
| 2,860,080 A * | 11/1958 | Wanamaker et al. | 148/238 |
| 3,257,363 A * | 6/1966 | Miller | B01J 19/0006 526/348.6 |
| 4,152,499 A | 5/1979 | Boerzel et al. | |
| 4,605,808 A | 8/1986 | Samson | |
| 5,068,490 A | 11/1991 | Eaton | |
| 5,182,333 A | 1/1993 | Powers et al. | |
| 5,910,550 A | 6/1999 | Rath | |
| 5,962,604 A | 10/1999 | Rath | |
| 6,642,329 B1 * | 11/2003 | Rath | 526/237 |
| 7,485,764 B2 | 2/2009 | Rath et al. | |
| 2006/0122447 A1 | 6/2006 | Rath et al. | |
| 2008/0214762 A1 | 9/2008 | Bode et al. | |
| 2008/0249264 A1 | 10/2008 | Hanefeld et al. | |
| 2011/0028666 A1 | 2/2011 | Mattmann et al. | |
| 2013/0041121 A1 | 2/2013 | König et al. | |

FOREIGN PATENT DOCUMENTS

| | | |
|---|---|---|
| EP | 0 489 508 A2 | 6/1992 |
| EP | 0 671 419 A1 | 9/1995 |
| EP | 0 807 641 A2 | 11/1997 |
| JP | 2005-539132 | 12/2005 |
| JP | 2009-501248 | 1/2009 |
| WO | WO 96/40808 A1 | 12/1996 |
| WO | WO 01/27172 A1 | 4/2001 |
| WO | 01/30869 A1 | 5/2001 |
| WO | 02/40553 A1 | 5/2002 |
| WO | WO 2005/028404 A1 | 3/2005 |
| WO | WO 2007/057406 A1 | 5/2007 |
| WO | WO 2007/096296 A1 | 8/2007 |
| WO | WO 2009/133187 A1 | 11/2009 |

OTHER PUBLICATIONS

Richards et al., "Measurement and control of polymerization reactors", Computers and Chemical Engineering 30, Elsevier, (2006), 1447-1463 (Year: 2006).*
International Search Report dated Mar. 19, 2013, in PCT/EP2013/050075 (with English Translation of Categories of Cited Documents).
U.S. Appl. No. 13/568,421, filed Aug. 7, 2012, US2013/0041121 A1, König, et al.
U.S. Appl. No. 13/597,703, filed Aug. 29, 2012, Hesse, et al.
U.S. Appl. No. 13/655,839, filed Oct. 19, 2012, Koenig, et al.
U.S. Appl. No. 13/765,031, filed Feb. 12, 2013, Wettling, et al.
Office Action, dated Oct. 11, 2016, corresponding to Japanese Patent application No. 2014-551576 with English Translation.

* cited by examiner

*Primary Examiner* — Philip Y Louie
(74) *Attorney, Agent, or Firm* — Grüneberg and Myers PLLC

(57) ABSTRACT

Continuous preparation of polyisobutylene having a content of terminal double bonds of more than 50% by polymerizing isobutene in the presence of a polymerization catalyst customary therefor, by combining a technical 1-butene-, 2-butene- and isobutene-containing $C_4$ hydrocarbon stream together with a stream of pure isobutene and feeding them into the reaction zone in such a way that the steady-state concentration of the isobutene in the combined stream at the feed point of the combined stream into the reaction zone has an average value of at least 40% by weight, and a polymerization plant therefor.

22 Claims, No Drawings

PROCESS FOR CONTINUOUSLY PREPARING POLYISOBUTYLENE

The present invention relates to an improved process for continuously preparing polyisobutylene having a content of terminal double bonds of more than 50% by polymerizing isobutene in the presence of a polymerization catalyst customary therefor. The present invention further relates to a polymerization plant for performing this process.

Polyisobutylene is obtained predominantly from technical $C_4$ hydrocarbon streams by controlled polymerization of the isobutene present therein—optionally after purification and/or concentration of the steam. These $C_4$ streams comprise typically, as well as isobutene, major amounts of 1-butene and 2-butene, and minor amounts of 1,3-butadiene; in addition, significant proportions of butanes are often present. Such isobutene-comprising $C_4$ hydrocarbon streams are, for example, $C_4$ raffinates such as "raffinate 2" and especially "raffinate 1", $C_4$ cuts from isobutane dehydrogenation, $C_4$ cuts from steamcrackers and from FCC crackers (fluid catalyzed cracking), provided that they have been substantially freed of 1,3-butadiene present therein. A $C_4$ hydrocarbon stream from an FCC refinery unit is also known as a "b/b" stream. Further suitable isobutene-comprising $C_4$ hydrocarbon streams are, for example, the product stream of a propylene-isobutane cooxidation or the product stream from a metathesis unit, which are generally used after customary purification and/or concentration. Suitable $C_4$ hydrocarbon streams comprise generally 3000 ppm by weight of butadienes or less. The presence of 1-butene and of cis- and trans-2-butene is substantially uncritical for the controlled polymerization of isobutene.

Typically, the concentration of isobutene in the $C_4$ hydrocarbon streams mentioned is in the range from 30 to 60% by weight. For instance, raffinate 1 consists generally of 30 to 50% by weight of isobutene, 10 to 50% by weight of 1-butene, 10 to 40% by weight of cis- and trans-2-butene, 2 to 35% by weight of butanes, and 20 to 2000 ppm by weight of butadienes. In the course of the polymerization process using raffinate 1, the unbranched butenes are generally virtually inert, and only the isobutene is polymerized.

WO 2007/096296 A1 describes a process for preparing polyisobutylene having a content of terminal double bonds of more than 50% from a wide variety of different technical $C_4$ hydrocarbon streams, in which the content of oxygenates in the hydrocarbon stream is reduced before the polymerization of the isobutene by contacting with an inorganic adsorbent at a pressure of 1 to 20 bar and a temperature of 20 to 220° C.

EP-A 671 419 discloses a process for preparing polyisobutylene, in which a virtually halogen-free polyisobutylene having a high content of terminal double bonds (vinylidene groups) is obtained by boron trifluoride-catalyzed polymerization of isobutene from a technical $C_4$ hydrocarbon stream, the 1-butene content of which has been depleted by a pretreatment step. Such a pretreatment step mentioned by way of example is selective hydroisomerization, which converts 1-butene to 2-butene.

WO 2005/028404 describes a process for preparing valeraldehyde by hydroformylating a $C_4$ hydrocarbon stream comprising 1-butene and at least 15% by weight of isobutene. The valeraldehyde can be converted further by aldol condensation and hydrogenation to 2-propylheptanol. The isobutene-enriched stream from the hydroformylation can be used, inter alia, for production of polyisobutylene.

The advantage of the direct use of technical $C_4$ hydrocarbon streams as "feed" in polyisobutene production compared to the use of pure isobutene is the elimination of the upstream process stage of isobutene extraction from such a technical hydrocarbon stream. The composition and particularly the content of isobutene in said technical $C_4$ hydrocarbon streams used as feed, however, changes permanently. For instance, the content of isobutene in such streams, usually supplied continuously, varies in the course of the reaction period by a few percent, usually in the order of magnitude of 5 to 10 percent, in the upward and downward direction. As a result, the specification of the polyisobutene produced also varies, more particularly the content of terminal double bonds (vinylidene groups) and the mean molecular weight, and also the residual content of monomers and/or oligomers, and the content of halogen in the polymer caused by a halogenated polymerization catalyst, for example a boron trifluoride complex.

It was an object of the present invention to develop a process which enables smoother operation of the isobutene polymerization from technical Ca hydrocarbon streams and ensures a homogeneous high content of terminal double bonds (vinylidene groups), a constant mean molecular weight, a homogeneous low consumption of polymerization catalyst and a low residual content of monomers and/or oligomers and of halogen in the polymer.

Accordingly, a process has been found for continuously preparing polyisobutylene having a content of terminal double bonds of more than 50% by polymerizing isobutene in the presence of a polymerization catalyst customary therefor, which comprises combining a technical 1-butene-, 2-butene- and isobutene-containing $C_4$ hydrocarbon stream which may comprise up to 3000 ppm by weight of 1,3-butadiene together with a stream of pure isobutene and feeding them into the reaction zone in such a way that the steady-state concentration of the isobutene in the combined stream at the feed point of the combined stream into the reaction zone has an average value of at least 40% by weight, especially an average value of at least 45% by weight, in particular an average value of at least 50% by weight.

Preferably, the process according to the invention has a steady-state concentration of isobutene in the combined stream at the feed point of the combined stream into the reaction zone, i.e. preferably an average value of 40 to 95% or 45 to 95% or 50 to 95% by weight, especially an average value of 40 to 80% or 45 to 80% or 50 to 80% by weight, in particular an average value of 40 to 65% or 45 to 65% or 50 to 65% by weight, more preferably an average value of 50 to 60% or 45 to 60% or 50 to 60% by weight, most preferably an average value of 40 to 55% or 45 to 55% or 50 to 55% by weight.

In a further preferred embodiment, the steady-state concentration of isobutene in the combined stream at the feed point of the combined stream into the reaction zone has a substantially constant value which may vary over the course of the polymerization reaction by a maximum of 10%, especially by a maximum of 8%, in particular by a maximum of 6%, more preferably by a maximum of 4%, most preferably by a maximum of 2%, in the upward or downward direction, based in each case on the mean isobutene concentration in the combined stream at the feed point.

A technical 1-butene-, 2-butene- and isobutene-containing $C_4$ hydrocarbon stream which may comprise up to 3000 ppm by weight of 1,3-butadiene and which is combined in accordance with the invention with a stream of pure isobutene and is suitable for use in the inventive polyisobutylene production is in principle any of the technical $C_4$ hydrocarbon streams enumerated at the outset. Preference is given for this purpose, however, to raffinate streams and streams analogous thereto. Such raffinate streams and analogous C$_4$ hydrocarbon streams are appropriately producible by four different methods:

In the first method, the C$_4$ hydrocarbon stream is provided by

Ia) in step Ia, subjecting naphtha or other hydrocarbon compounds to a steamcracking or FCC process and, from the stream formed, removing a C$_4$ olefin mixture which comprises 1-butene, 2-butene, isobutene and more than 1000 ppm by weight of butadienes, with or without butynes, and IIa) preparing from the C$_4$ olefin mixture formed in step Ia a C$_4$ hydrocarbon stream (usually referred to as raffinate 1) consisting essentially of 1-butene, 2-butene and isobutene, with or without butanes, by hydrogenating the butadienes and butynes to butenes or butanes by means of selective hydrogenation, or removing the butadienes and butynes by extractive distillation to such an extent that the content of 1,3-butadiene is not more than 1000 ppm by weight.

In the second method, the C$_4$ hydrocarbon stream is provided by

Ib) in step Ib, preparing from a hydrocarbon stream comprising butanes by dehydrogenation and subsequent purification, a C$_4$ olefin mixture which comprises 1-butene, 2-butene, isobutene and more than 1000 ppm by weight of butadienes, with or without butynes and with or without butanes, and IIb) preparing from the C$_4$ olefin mixture formed in step Ib a C$_4$ hydrocarbon stream (usually referred to as raffinate 1) consisting essentially of 1-butene, 2-butene and isobutene, with or without butanes, by hydrogenating the butadienes and butynes to butenes or butanes by means of selective hydrogenation, or removing the butadienes and butynes by extractive distillation to such an extent that the content of 1,3-butadiene is not more than 1000 ppm by weight.

In the third method, the C$_4$ hydrocarbon stream (typically in the form of raffinate 2) is provided by Ic) preparing from methanol by dehydrogenation a C$_4$ olefin mixture (MTO process) which comprises 1-butene, 2-butene and isobutene, with or without butadienes, alkynes, and with or without butanes, and IIc) freeing the C$_4$ olefin mixture of butadienes or alkynes by distillation, selective hydrogenation or extractive distillation.

In the fourth method, the C$_4$ hydrocarbon stream is provided by

Id) in step Id, preparing from a hydrocarbon stream comprising olefins by metathesis conversion and, if necessary, subsequent purification a C$_4$ olefin mixture which comprises 1-butene, 2-butene and isobutene, with or without butadienes and with or without butynes, and IId) preparing from the C$_4$ olefin mixture formed in step Id a C$_4$ hydrocarbon stream consisting essentially of 1-butene, 2-butene and isobutene, with or without butanes, by hydrogenating the butadienes and butynes to butenes or butanes by means of selective hydrogenation, or removing the butadienes and butynes by extractive distillation to such an extent that the content of 1,3-butadiene is not more than 1000 ppm by weight.

"2-Butene" is understood here to mean both cis- and trans-2-butene and mixtures thereof.

Raffinate 2 has essentially the same composition as raffinate 1, apart from the fact that raffinate 2 comprises smaller amounts of isobutene. Typically, raffinate 2 has amounts of less than 10% by weight of isobutene.

The fourth method comprising steps Id and IId typically provides C$_4$ hydrocarbon streams having an isobutene content of 70 to 95% by weight, especially 80 to 90% by weight; the remainder is essentially other butenes and other inert hydrocarbons. The starting material used as hydrocarbon streams comprising olefins in step Id is generally an olefin mixture which consists essentially of ethylene and 2-butene and, in the metathesis conversion, as well as propene as the main product, also affords isobutene; after removal of the propene, the remaining hydrocarbon stream consists predominantly of isobutene.

The extractive distillation in step IIa, IIb, IIc or IId is preferably carried out with a butadiene-selective solvent selected from the class of the polar aprotic solvents, for example acetone, furfural, acetonitrile, dimethylacetamide, dimethylformamide or N-methylpyrrolidone.

The selective hydrogenation in step IIa, IIb, IIc or IId can be used for a substantial reduction of diolefins and acetylenic compounds, since these compounds could impair the subsequent process stages. In addition, the selective hydrogenation of a relatively large amount of 1,3-butadiene can also considerably increase the amount of linear monoolefins, which increases the production capacity of subsequent stages. Suitable catalysts and methods (for example relating to the hydrogen supply) allow the 1-butene to 2-butene ratio in the selective hydrogenation to be controlled within certain limits (known as hydroisomerization). The target is 1-butene to 2-butene ratios of at least 1:3, preferably of at least 2:3, more preferably of more than 1:1. The component step of selective hydrogenation is preferably carried out in the liquid phase over a metal selected from the group of nickel, palladium and platinum on a support, preferably palladium on alumina, at a temperature of 20 to 200° C., a pressure of 1 to 50 bar, a volume flow rate of 0.5 to 30 m$^3$ of fresh feed per m$^3$ of catalyst per hour, and a ratio of recycle to feed stream of 0 to 30, with a molar ratio of hydrogen to diolefins of 0.5 to 50.

When the content of 1,3-butadiene in the C$_4$ olefin mixture obtained in step Ia, Ib, Ic or Id is 5% by weight or more, the content of 1,3-butadiene is typically lowered by means of extractive distillation to a content between 1000 ppm by weight and 5% by weight, and the content of 1,3-butadiene is subsequently lowered further to 1000 ppm by weight or less by means of selective hydrogenation.

The technical C$_4$ hydrocarbon stream to be used in the polymerization of the isobutene preferably has a 1-butene to 2-butene volume ratio of 3:1 to 1:3.

The content of 1,3-butadiene in the technical C$_4$ hydrocarbon stream to be used in the polymerization of isobutene is preferably less than 2000 ppm by weight, more preferably less than 1000 ppm by weight, in particular 100 ppm by weight.

In general, the technical C$_4$ hydrocarbon stream which is to be used in the polymerization of isobutene and is preferably a raffinate 1 stream comprises 2 to 35% by weight, preferably 5 to 30% by weight, of butanes, 10 to 40% by weight, preferably 10 to 30% by weight, of 2-butene, 10 to 50% by weight, preferably 15 to 35% by weight, of 1-butene, 30 to 50% by weight, preferably 35 to 45% by weight, of isobutene, and 20 to 3000 ppm by weight, preferably 20 to less than 2000 ppm by weight, especially 20 to 1000 ppm by weight, of butadienes.

In a preferred embodiment of the present invention, in the provision of the technical 1-butene-, 2-butene- and isobutene-containing C$_4$ hydrocarbon stream used in the polymerization of isobutene, which may comprise up to 3000 ppm by weight of 1,3-butadiene and which is combined in accordance with the invention with a stream of pure isobutene, a hydroformylation of the $C_4$ hydrocarbon stream obtained from step IIa or IIb or IId is carried out as an additional step III in the presence of a customary hydroformylation catalyst with hydrogen and carbon monoxide, and the $C_5$ aldehydes formed are removed from the resulting $C_4$ hydrocarbon stream.

This hydroformylation can generally be carried out in the manner known and customary to the person skilled in the art. The hydroformylation of 1-butene leads to n-valeraldehyde, the main constituent in the $C_5$ aldehyde mixture formed in the hydroformylation stage of the abovementioned process. In the hydroformylation, n-valeraldehyde (n-pentanal) is prepared under transition metal catalysis from the 1-butene with addition of synthesis gas (carbon monoxide-hydrogen mixture, typically in a volume ratio of 3:1 to 1:3). Structurally isomeric $C_5$ aldehydes can form in small amounts from other components of the $C_4$ starting stream.

The catalysts used for the hydroformylation reaction are generally rhodium complexes with phosphorus-comprising ligands. Such ligands are typically a mono- or diphosphine, especially a triarylphosphine such as triphenylphosphine. The hydroformylation reaction is carried out typically at temperatures of 50 to 150° C., preferably 70 to 120° C., and at pressures of 5 to 50 bar, preferably 10 to 30 bar.

The $C_4$ hydrocarbon stream after the hydroformylation (usually referred to as raffinate 1P) comprises typically 2 to 25% by weight, preferably 5 to 20% by weight, of butanes, 25 to 70% by weight, preferably 35 to 55% by weight, of 2-butene, 1 to 15% by weight, preferably 3 to 10%, by weight of 1-butene, 30 to 55% by weight, preferably 35 to 50% by weight, of isobutene and 20 to 1000 ppm by weight, preferably 20 to less than 300 ppm by weight, of butadienes. The volume ratio of 1-butene to 2-butene in this $C_4$ stream is typically 1:3 to 1:60.

The polymerization of the isobutene itself can be carried out after a conditioning step by means of an inorganic adsorbent as described in WO 2007/096296, in the customary manner known to those skilled in the art. The prior art which is representative in this regard is reflected, for example, by the documents U.S. Pat. Nos. 4,152,499, 4,605, 808, 5,068,490, EP-A 489 508 and EP-A 671 419.

The polymerization catalyst used for isobutene is preferably a homogeneous or heterogeneous catalyst from the class of the Brønsted or Lewis acids. In particular, this catalyst is boron trifluoride or boron trifluoride complexes such as boron trifluoride etherates, e.g. boron trifluoride diethyl etherate, or boron trifluoride-alcohol complexes, for example with methanol, ethanol, isopropanol or sec-butanol. Tin tetrachloride too, either alone or together with mineral acids or alkyl halides such as tert-butyl chloride as cocatalysts, and also aqueous aluminum chloride, may be used as polymerization catalysts.

The polymerization catalyst used for isobutene may additionally also comprise complexes of aluminum trihalides such as aluminum trichloride or alkylaluminum halides or of iron halides such as iron(III) chloride with donors such as alkyl carboxylates, or especially dialkyl ethers such as dibutyl ether, optionally in the presence of an initiator such as an alcohol, a phenol or water. Another useful polymerization catalyst for isobutene has been found to be the complex of a Lewis acid such as aluminum trichloride or iron(III) chloride and a donor such as dibutyl ether, in the presence of an organic sulfonic acid such as methanesulfonic acid as an initiator.

The polymerization catalyst is generally used in amounts of 0.001 to 10% by weight, in particular 0.01 to 1% by weight, based on the isobutene content of the $C_4$ hydrocarbon stream used.

The isobutene polymerization is carried out typically at temperatures of −100 to +100° C., especially −50 to +25° C., in particular −35 to +5° C. Appropriately a pressure of 10 to 5000 kPa is employed.

The polymerization reaction is appropriately terminated by adding excess amounts of water or of basic material, for example gaseous or aqueous ammonia or aqueous alkali metal hydroxide solution such as sodium hydroxide solution. After unconverted $C_4$ monomers have been removed, the crude polymerization product is typically washed repeatedly with distilled or deionized water, in order to remove adhering inorganic constituents. To achieve high purities or to remove undesired low and/or high molecular weight fractions, the polymerization product can be fractionally distilled under reduced pressure.

The polymerization process according to the invention achieves essentially halogen-free polyisobutylene having a high content of terminal double bonds (vinylidene groups) of more than 50%, preferably of at least 65%, especially of at least 75%, especially of at least 80%. The residual content of halogen, which is typically present as fluoride or chloride depending on the polymerization catalyst used, is usually less than 150 ppm by weight, especially less than 100 ppm by weight, in particular less than 75 ppm by weight.

The polyisobutylene thus prepared generally has a number-average molecular weight $M_n$ of 500 to 5000, especially 700 to 3500, in particular 750 to 3000, in each case measured by gel permeation chromatography (GP). The polydispersity ($D=M_w/M_n$) is typically less than 2.5, preferably less than 2.0 and especially 1.8 or less.

The present invention also provides a polymerization plant for continuously preparing polyisobutylene having a content of terminal double bonds of more than 50% by polymerizing isobutene in the presence of a polymerization catalyst customary therefor, comprising a temperature-controllable reaction zone for the performance of the polymerization reaction, feed devices and removal devices, wherein the polymerization plant comprises a feed device into the reaction zone for a combined stream of a technical 1-butene-, 2-butene- and isobutene-containing $C_4$ hydrocarbon stream which may comprise up to 3000 ppm by weight of 1,3-butadiene, and a stream of pure isobutene.

The feed device for the combined stream of the technical $C_4$ hydrocarbon stream and the stream of pure isobutene of the inventive polymerization plant preferably comprises a regulating device which ensures that the steady-state concentration of isobutene in the combined stream at the feed point of the combined stream into the reaction zone has an essentially constant value which may vary over the course of the polymerization reaction by a maximum of 10%, especially by a maximum of 8%, in particular by a maximum of 6%, more preferably by a maximum of 4%, most preferably by a maximum of 2%, in the upward or downward direction, based in each case on the mean isobutene concentration in the combined stream at the feed point.

For production of the mixture of the stream of pure isobutene with the $C_4$ hydrocarbon stream, it is possible in principle to use all customary feed devices. The mixing can be effected either in continuous mode or in batchwise mode with subsequent continuous feeding of the mixture thus produced into the reaction zone. In either option, the mixing can be effected, in terms of process technology, by static or dynamic principles.

"Continuous mode" is understood here to mean the constant supply of the two reactants via pipelines into a mixing unit and further conduction into the process steps which follow. The mixing can be obtained by static mixing apparatuses such as T-pieces, nozzles, orifice plates, static mixers, or by dynamic mixing apparatuses such as mixing pumps or stirred tanks.

"Batchwise mode" is understood here to mean the production of mixtures directly in batch vessels by dynamic mixing apparatuses, i.e. by mixing by means of a stirrer or by pumped circulation, or pumped circulation with static mixing elements such as static mixers or nozzles in pumped circulation, by static mixing apparatuses such as static mixers, nozzles, orifice plates or T-pieces in the feed of the batch vessel, or by dynamic mixing apparatuses such as mixing pumps or stirred tanks. After production of a mixed batch, it is passed on into the continuous process steps downstream.

In terms of process technology, an essentially constant isobutene concentration in the stream fed into the reaction zone can in principle be established by means of all regulating devices customary therefor. Typically, a target value is set for the isobutene concentration to be established, online analysis is used to measure the respective isobutene concentrations in the $C_4$ hydrocarbon stream and in the resulting stream after the mixing with the pure isobutene stream, and the regulating device is used, in a permanently dynamic manner, via control elements, for control, i.e. closed-loop control, of the flows of $C_4$ hydrocarbon stream and pure isobutene stream through the feed devices.

The technical equipment used for this purpose normally includes regulation circuits comprising mass flow meters, which usually work by a heat, coriolis force or eddy current measurement principle, and control elements such as regulating valves, regulating ball valves or ball valves in the streams. Alternatively, it is also possible to dispense with the mass flow meter in the $C_4$ input stream and replace it with a mass flow meter in the overall stream.

The examples which follow are intended to illustrate the present invention without restricting it.

EXAMPLES 1 TO 8

Examples 1 to 8 which follow were conducted in a continuous polymerization apparatus consisting of a jacket-cooled reactor with a capacity of 800 ml, a mechanical stirrer, a raw material input tube with precooling of the raw material, with a separate inlet tube for gaseous boron trifluoride, a dropping funnel for the methanol added and a stub for the continuous discharge of the reactor contents.

The raw material added via the raw material input tube originated from a mixing vessel cooled to the reaction temperature of −17° C., in which, as appropriate, raffinate 1 of quality A and of quality B and pure isobutene were initially charged in different amounts and mixed by means of a stirrer.

The composition of the raffinate 1 qualities was as follows:

|  | Raffinate 1 A ("R1A") | Raffinate 1 B ("R1B") |
|---|---|---|
| Isobutene | 36.1% by wt. | 45.7% by wt. |
| 1-Butene | 35.4% by wt. | 27.3% by wt. |
| trans-2-Butene | 8.4% by wt. | 7.1% by wt. |
| cis-2-Butene | 5.8% by wt. | 4.2% by wt. |
| Isobutane | 4.1% by wt. | 3.4% by wt. |
| n-Butane | 10.2% by wt. | 11.0% by wt. |
| Butadiene | 285 ppm by wt. | 741 ppm by wt. |

The pure isobutene used ("P-IB") had a purity of >99.8% by weight (<0.1% by weight of n-butenes; <0.05% by weight of butanes; <40 ppm by weight of alcohols).

The reaction was conducted in each case at reactor interior temperature −17° C. and a boron trifluoride/methanol addition of 6.1 g/h of $BF_3$/3.8 g/h of methanol. The flow rate (corresponding to the raw material input rate=crude product discharge rate) was 7 l/h (approx. 4.4 kg/h), and the mean residence time in the reactor at a fill level of 500 ml was correspondingly approx. 4.3 minutes.

The initially still-cold reactor output was passed into an excess of demineralized water at approx. 50° C. and mixed vigorously. The amount of hot water was selected such that the mixing temperature of the two phases was approx. 20° C. This already evaporated a portion of the solvent (unconverted $C_4$ hydrocarbons). After approx. 20 minutes of residence time for settling of the two phases, the upper (organic) phase was removed and product samples were freed of the residual solvent in a rotary evaporator for the analysis.

The table below shows the results of the eight polymerization runs [content of residual isobutene in the product in % by weight ("R") number-average molecular weight $M_n$, content of vinylidene groups in % ("α"), polydispersity ("D") and residual fluorine content in the product in ppm by weight ("F")] as a function of the mean isobutene concentration at the feed point of the reactor ("m-IB") and the variations in the m-IB in the upward or downward direction ("$S_a$", measured in absolute % by weight, and "$S_r$", measured in relative %, based in each case on the m-IB).

| Example No. | Raw material [% by wt.] | m-IB | R | $S_a$ | $S_r$ | $M_n$ | α | D | F |
|---|---|---|---|---|---|---|---|---|---|
| 1 | 100 R1A | 36.1 | 3.8 | 0 | 0 | 934 | 71.2 | 1.8 | 127 |
| 2 | 100 R1B | 45.7 | 3.8 | 0 | 0 | 1187 | 77.8 | 1.7 | 97 |
| 3 | 50.0 R1A + 50.0 R1B | 40.9 | 3.9 | 0 | 0 | 1009 | 76.9 | 1.7 | 111 |
| 4* | 50.0 R1A + 50.0 R1B | 40.9 | 3.9 | 4.8 | 11.7 | 1076 | 72.8 | 2.1 | 123 |
| 5 | 78.2 R1A + 21.8 P-IB | 50.0 | 4.1 | 0 | 0 | 1193 | 81.2 | 1.7 | 68 |
| 6 | 92.1 R1B + 7.9 P-IB | 50.0 | 4.0 | 0 | 0 | 1211 | 82.3 | 1.7 | 57 |

-continued

| Example No. | Raw material [% by wt.] | m-IB | R | $S_a$ | $S_r$ | $M_n$ | α | D | F |
|---|---|---|---|---|---|---|---|---|---|
| 7** | 50.0 No. 5 + 50.0 No. 6 | 50.0 | 4.1 | 0 | 0 | 1187 | 81.9 | 1.7 | 59 |
| 8*** | 50.0 No. 5 + 50.0 No. 6 | 50.0 | 4.2 | 0 | 0 | 1226 | 80.8 | 1.8 | 63 |

"R" was determined by headspace GC and indicates the proportion of unconverted isobutene in the vaporizable product mixture immediately after the mixing of the reactor discharge with water.
"α" indicates the content of vinylidene groups of all carbon-carbon double bonds in the polyisobutene obtained and was determined by means of $^1$H NMR spectroscopy.
"D" was determined by GPC.
N.B.:
*In comparative example No. 4, in continuous operation, the raffinate 1 of qualities A and B used as the raw material was alternated every 5 minutes, but used to an extent of 100% within any 5-minute interval. The product specimen analyzed was collected over a period of 30 minutes, mixed and worked up as described above. This operation simulated a raw material stream whose composition changed several times over the course of time. Comparison with example No. 3, in which both raffinate 1 qualities were mixed beforehand, shows the influence of a raw material composition varying over time on the product quality.
**In example No. 7, a mixture of the raw materials of examples No. 5 and No. 6 was premixed in proportions by weight of 50:50 and used.
***In example No. 8, the mixture of raw materials of examples No. 5 and No. 6 was used, but not in premixed form; instead, the respective raw material from example No. 5 or No. 6 was used with alternation every 5 minutes. The product specimen was collected over a period of 30 minutes and mixed vigorously before workup.

The invention claimed is:

1. A process for continuously preparing polyisobutylene having a content of terminal double bonds of more than 50% by polymerizing isobutene in the presence of a polymerization catalyst customary therefor, the process comprising:
combining (i-a) a technical 1-butene-, 2-butene- and isobutene-containing $C_4$ hydrocarbon stream and/or (i-b) a $C_4$ cut from isobutane dehydrogenation, comprising 0 to 3000 ppm by weight of 1,3-butadiene, together with a stream of pure isobutene and feeding them into a reaction zone in such a way that a steady-state concentration of the isobutene in the combined stream at a feed point of the combined stream into the reaction zone has an average value of at least 40 wt. %;
wherein the steady-state concentration of isobutene in the combined stream at the feed point of the combined stream into the reaction zone is controlled, by varying the flow rate of the stream of pure isobutene, to have a substantially constant value which may vary by a maximum of 10% in the upward or downward direction over the course of the polymerization reaction, based on the steady-state concentration of isobutene in the combined stream at the feed point.

2. The process of claim 1, wherein the steady-state concentration of isobutene in the combined stream at the feed point of the combined stream into the reaction zone has an average value in a range of 40 to 60 wt. %.

3. The process of claim 1, wherein the steady-state concentration of isobutene in the combined stream at the feed point of the combined stream into the reaction zone has a substantially constant value which may vary by a maximum of 8% in the upward or downward direction over the course of the polymerization reaction, based on the steady-state concentration of isobutene in the combined stream at the feed point.

4. The process of claim 1, wherein the steady-state concentration of isobutene in the combined stream at the feed point of the combined stream into the reaction zone has a substantially constant value which may vary by a maximum of 6% in the upward or downward direction over the course of the polymerization reaction, based on the steady-state concentration of isobutene in the combined stream at the feed point.

5. The process of claim 1, wherein the steady-state concentration of isobutene in the combined stream at the feed point of the combined stream into the reaction zone has a substantially constant value which may vary by a maximum of 4% in the upward or downward direction over the course of the polymerization reaction, based on the steady-state concentration of isobutene in the combined stream at the feed point.

6. The process of claim 1, wherein the isobutene-containing $C_4$ hydrocarbon stream comprises less than 2000 ppm of 1,3-butadiene.

7. The process of claim 1, wherein the isobutene-containing $C_4$ hydrocarbon stream comprises less than 1000 ppm of 1,3-butadiene.

8. The process of claim 1, wherein the polymerization catalyst is at least one polymerization catalyst selected from the group consisting of boron trifluoride, a boron trifluoride complex, tin tetrachloride and aqueous aluminum chloride.

9. The process of claim 1, wherein the polymerization catalyst is used in an amount of from 0.001 to 10 wt. % based on the isobutene content of the $C_4$ hydrocarbon stream.

10. The process of claim 1, wherein the isobutene polymerization is carried out at a temperature in a range of from −100 to +100° C.

11. The process of claim 1, wherein the isobutene polymerization is carried out at a temperature in a range of from −50 to +25° C.

12. The process of claim 1, wherein the isobutene polymerization is carried out at a temperature in a range of from −35 to +5° C.

13. The process of claim 1, wherein the polyisobutylene has a content of terminal double bonds of at least 65%.

14. The process of claim 1, wherein the polyisobutylene has a content of terminal double bonds of at least 75%.

15. The process of claim 1, wherein the polyisobutylene has a content of terminal double bonds of at least 80%.

16. The process of claim 1, wherein the polyisobutylene has a polydispersity index of less than 2.5.

17. The process of claim 1, wherein the polyisobutylene has a polydispersity index of less than 2.0.

18. The process of claim 1, wherein the polyisobutylene has a polydispersity index of less than 1.8.

19. The process of claim 1, wherein the technical 1-butene-, 2-butene- and isobutene-containing $C_4$ hydrocarbon stream and/or the $C_4$ cut from isobutane dehydrogenation, comprising 0 to 3000 ppm by weight of 1,3-butadiene is combined with the stream of pure isobutene and fed into the reaction zone in such a way that the steady-state concentration of isobutene in the combined stream at the feed point of the combined stream into the reaction zone has an average value of at least 45 wt. %.

20. The process of claim 1, wherein the technical 1-butene-, 2-butene- and isobutene-containing $C_4$ hydrocarbon stream and/or the $C_4$ cut from isobutane dehydrogenation, comprising 0 to 3000 ppm by weight of 1,3-butadiene is combined with the stream of pure isobutene and fed into the reaction zone in such a way that the steady-state concentration of isobutene in the combined stream at the feed point of the combined stream into the reaction zone has an average value of at least 50 wt. %.

21. The process of claim 18, wherein the polyisobutene has an $M_n$ in a range of from 500 to 5000.

22. The process of claim 1, wherein the polyisobutylene has a residual halogen content less than 123 ppm by weight.

* * * * *